United States Patent [19]

Golias

[11] 4,360,418
[45] Nov. 23, 1982

[54] ELECTROPHORESIS AND STAINING APPARATUS

[75] Inventor: Tipton L. Golias, Beaumont, Tex.

[73] Assignee: Helena Laboratories Corporation, Beaumont, Tex.

[21] Appl. No.: 273,147

[22] Filed: Jun. 12, 1981

[51] Int. Cl.³ .............................................. G01N 27/26
[52] U.S. Cl. ........................ 204/299 R; 204/180 G; 424/12; 23/230 B
[58] Field of Search ........................ 204/299 R, 180 G

[56] References Cited
U.S. PATENT DOCUMENTS 4,059,501  11/1977  Strickler ........................ 204/299 R
4,124,470  11/1978  Dahms ........................... 204/180 G Primary Examiner—John F. Niebling
Attorney, Agent, or Firm—Cullen, Sloman, Cantor, Grauer, Scott & Rutherford

[57] ABSTRACT

An automated electrophoresis and staining apparatus provides a platform spaced above a base. An electrophoresis chamber and a series of vats are mounted upon the platform and arranged in a row, the vats being adapted to contain respectively a liquid stain and a series of plate processing solutions. A plate holder rack having a horizontal open frame supports an upright electrophoresis plate onto which has been applied a sample for electrophoretic fractionization. The plate is nested within the chamber within an electrophoretic circuit for a predetermined period. A power operated lift and transfer assembly upon the base is adapted to lift, transfer and lower the plate holder rack and plate from the chamber and progressively into each of the underlying vats for a predetermined period in a linear stepping motion, maintaining the plate in an upright position at all times.

23 Claims, 5 Drawing Figures

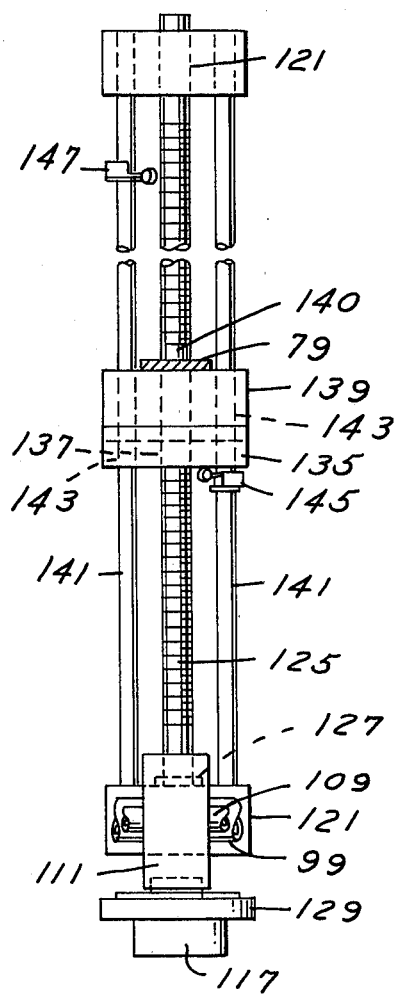
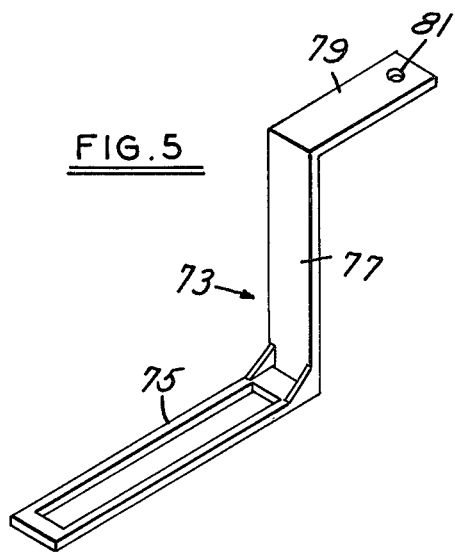
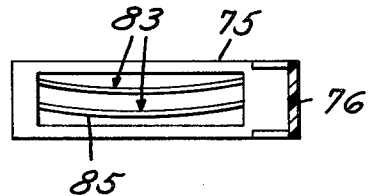

ELECTROPHORESIS AND STAINING APPARATUS

BACKGROUND OF THE INVENTION

Prior Art

In the diagnosing of ailments of persons and animals, it is known that much information can be provided by an analysis of certain biological fluids such as serum proteins, lipoproteins, hemoglobin and isoenzymes. Electrophoresis as a method of separating the respective ingredients of said fluids, for a microscopic analysis or employing optical densitometry is known and shown or disclosed in one or more of the following patents:

| UNITED STATES PRIOR ART | | |
|---|---|---|
| 3,607,695 | Schneider | 9/21/71 |
| 3,759,773 | Dwyer et al | 9/18/73 |
| 3,808,118 | Golias | 4/30/74 |
| 3,873,433 | Seidel, et al | 3/25/75 |
| 3,884,764 | Goodhue | 5/20/75 |
| 3,907,642 | William Richmond | 9/23/75 |
| 3,907,645 | William Richmond | 9/23/75 |
| 3,912,610 | Kingdon Lou | 10/14/75 |
| BRITISH PRIOR ART | | |
| 1,060,874 | Stanton | (1966) |
| 1,211,008 | Elevitch | (1967) |
| 1,212,844 | Stanton | (1967) |
| 1,385,319 | William Richmond | (1972) |
| 1,385,320 | William Richmond | (1972) |
| 1,466,040 | Behringwerke Aktiengesellschaft | (1975) |

In the basic method of electrophoresis, charged molecules of fluids are separated under the influence of an electrical field wherein the sample of solution to be examined is mounted upon a support medium having a buffer moistened porous surface. Since the various components move at different rates, laterally through the support media, the sample may be separated into its respective elements. The subsequent staining of the fractions prepare the plate when dried for examination by optical densitometry or other methods.

RELATED APPLICATION

Copending herewith is U.S. patent application Ser. No. 273,162, filed June 12, 1981, executed of even date, entitled Automated Electrophoresis Apparatus and Method.

SUMMARY OF THE INVENTION

An important feature of the present invention is to provide an automated electrophoresis and staining apparatus wherein an electrophoresis plate has applied thereto a sample for electrophoretic fractionization and supported in an upright position by a transfer frame so that the plate may be projected downwardly into an electrophoresis chamber for a predetermined period within an electrophoretic circuit.

A further feature is the provision in conjunction with the electrophoresis chamber of a plurality of solution containing vats arranged in a line upon a platform such that the plate may be transferred to a vat containing a stain solution and successively to other processing solutions, at all times maintaining the plate in an upright position.

A further feature includes a plate holder rack which has a horizontal frame adapted for supporting one or a plurality of electrophoresis plates in registry with the underlying chamber and vats.

A further feature is the provision of an electrophoresis chamber having a hinged cover within which the plate holder rack and the plates are supported which includes an electrical circuit with conductors and the use of conductive buffer moistened sponges in registry with the top and bottom edges of the plates for completing an electrical circuit through the electrophoresis plates.

A further feature includes a power operated lift and transfer assembly adapted to progressively lift, transfer and lower the plate holder rack and the plates from the chamber and progressively into each of the underlying vats for a predetermined period successively in a linear stepping motion, with the plates maintained at all times in an upright position.

A further feature is the specific electrophoresis chamber wherein an electrophoretic circuit is provided upon the interior thereof protectively enclosed by a pivoted cover and after a predetermined period, a power operated lift and transfer assembly on elevation automatically opens the cover so as not to block the upward movement of the rack and plates suspended therefrom.

A further feature is to provide automated electrophoresis and staining apparatus which includes the process of electrophoresis and necessary sample staining into a continuous operation.

A further feature of the present invention of the timing of the electrophoresis process may be predetermined depending upon the sample being fractionated wherein the voltage applied may be modified for a particular electrophoresis depending upon the nature of this sample tested. The interval of immersion within the respective vats may be preset according to a predetermined program or may be manually controlled.

A further feature includes a method of electrophoresis wherein there is included the step of supporting in an upright position a nonconductive plate having on one surface a buffer moistened electrophoresis media to which has been applied a sample selected from the group consisting of serum proteins, lipoproteins, hemoglobin and isoenzymes. Enclosing of the plate within an electrophoresis chamber after applying an electrical potential to the plate ends within an electrical power circuit for a predetermined period at a predetermined voltage, wherein the specimen elements fractionate and migrate laterally through portions of the media and after staining, is available for analysis by optical densitometry or other methods.

These and other objects will be seen from the following specification and claims in conjunction with the appended drawings.

THE DRAWINGS

FIG. 3 is a vertical section taken in the direction of arrows 3—3 of FIG. 2.

FIG. 4 is a fragmentary section taken in the direction of arrows 4—4 of FIG. 2 showing the plate holder rack.

FIG. 5 is a perspective view of the plate holder rack as further shown in FIG. 2.

It will be understood that the above drawings illustrate merely a preferred embodiment of the invention including the apparatus and the method employed, and that other embodiments are contemplated within the scope of the claims hereafter set forth.

DETAILED DESCRIPTION OF AN EMBODIMENT OF THE INVENTION

Figure 1:
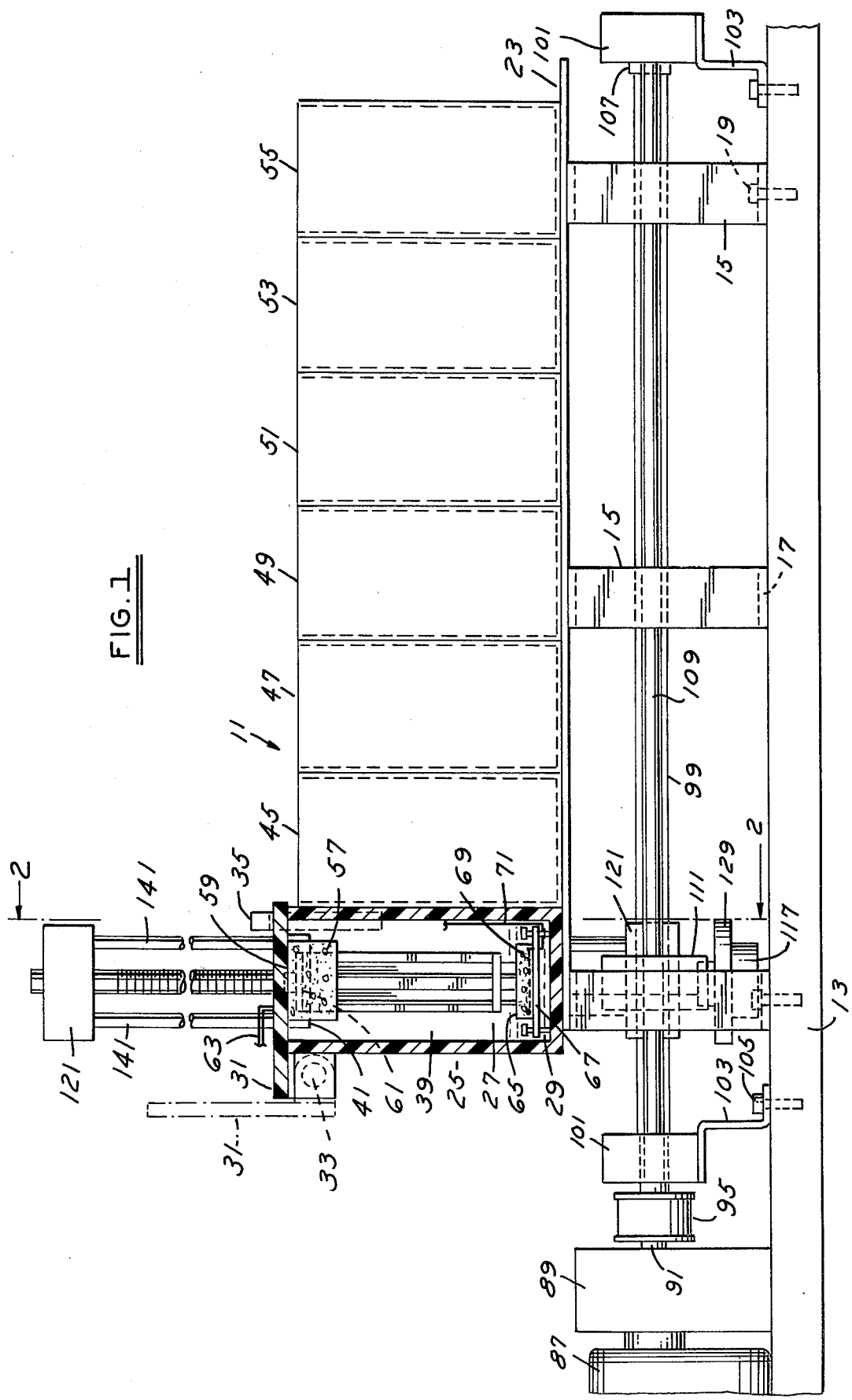
FIG. 1 is a partly sectioned fragmentary side elevational view of the present automated electrophoresis and staining apparatus.
Figure 2:
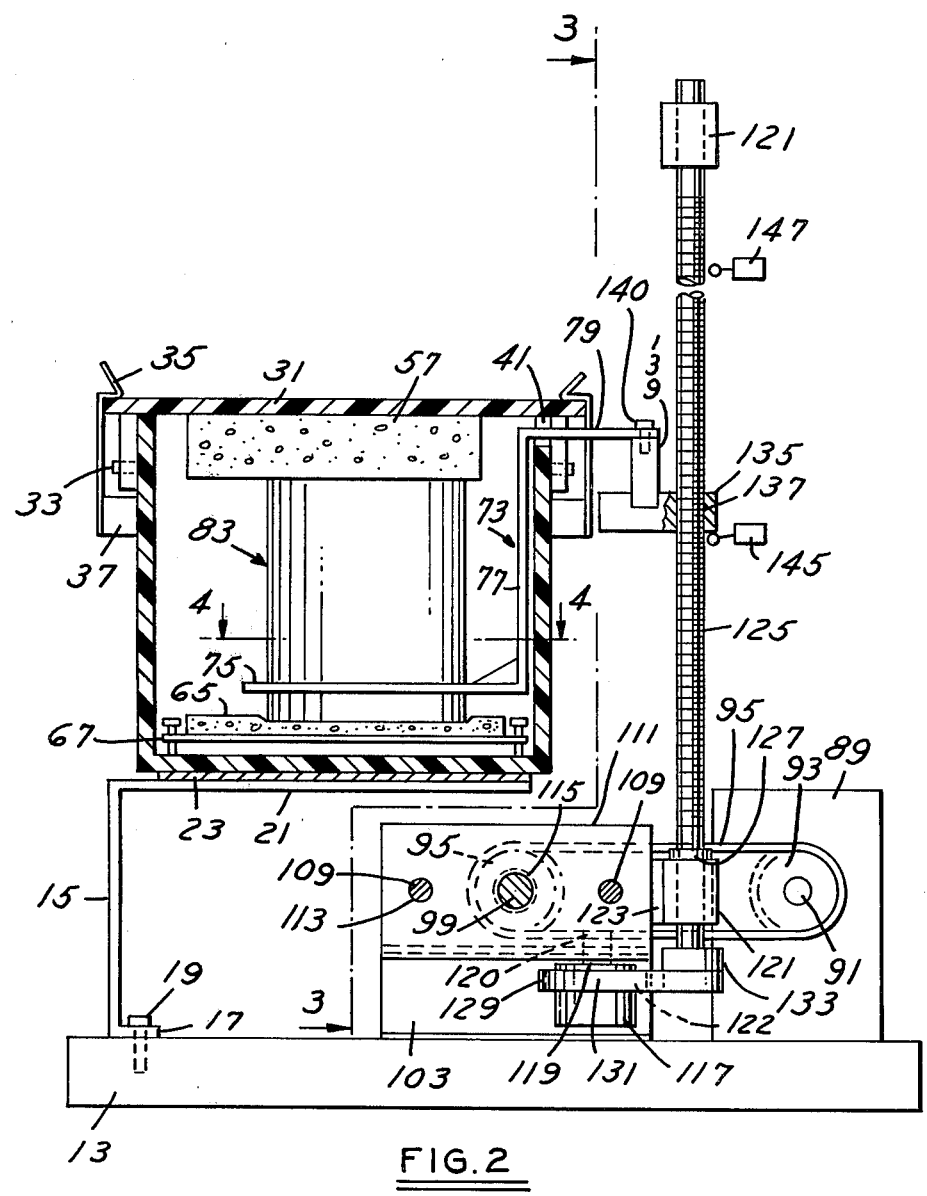
FIG. 2 is a vertical section taken in the direction of arrows 2—2 of FIG. 1.

The present automated electrophoresis and staining apparatus, is generally indicated at 11, FIG. 1 and includes an elongated base 13 upon which are mounted a series of longitudinally spaced transverse brackets 15 secured by fasteners 19 to the base and including mount flange 17, FIG. 2.

Spaced above said base and mounted upon the respective support arms 21 of said brackets is an elongated platform 23 suitably secured thereto.

Mounted upon platform 23 is a plastic container 25 defining an electrophoresis chamber 27 adapted to contain a suitable buffer solution 29 and having cover 31 hinged thereto at 33.

During the period of electrophoresis within chamber 27, cover 31 remains in a closed position as retained by the resilient hold down clips 35 anchored at 37, FIG. 2. The cover remains closed for a predetermined interval and thereafter is automatically moved to the open position shown in dash lines in FIG. 1 when the plate support rack 73 is elevated by a lift and transfer mechanism to which it is attached. One end wall 39 of the electrophoresis chamber is notched at its upper end at 41 through which a portion of the plate holding rack 73 projects as in FIG. 2.

A series of vats, preferably constructed of an inert material, such as a plastic, are mounted upon platform 23, side by side and arranged in a row and aligned with chamber 25. These vats are adapted to contain respectively a liquid stain as in the first vat 45, a first rinse solution in vat 47, FIG. 1, a second rinse solution in vat 49, a third rinse solution in vat 51, a fixative solution in vat 53 and a final rinse solution in vat 55.

ELECTROPHORESIS CHAMBER

The electrophoresis chamber 27 within container 25 suspends along the undersurface of cover 31, a buffer moistened conductive sponge 57 connecting the cover as at 59, FIG. 1 and in contact with and overlying an elongated platinum electrode 61 connected by lead 63 to a suitable power source.

Within a quantity of buffer solution upon the bottom of said container 25, there is provided a buffer moistened conductive sponge 65 retained upon the vertically adjustable elongated sponge support 67. Adjacent the lower surface of the sponge and in electrical contact therewith is an elongated platinum electrode 69 which by the lead 71 is adapted to complete the electrophoretic circuit within said chamber. The buffer moistened sponge 65 is partly immersed within the buffer solution 29. One example of a buffer solution is: Barbital 1.84 gm, Sodium Barbital 10.30 gm dissolved in one liter of water.

Plate holder rack 73, FIGS. 1, 2, 3 and 4 is constructed of MYLAR (Trademark) or other non-conductive plastic material and includes an elongated horizontal rectangular open frame 75 which at one end terminates in the upright support arm 77 which at its upper end terminates in the top plate 79. Said plate projects through notch 41 in the end wall 39 of container 25 and includes at its end an aperture 81 to receive the fastener 140 for securing the plate holder rack to the block 139 connected to the lift and transfer mechanism hereafter described. One or a series of parallel spaced rectangular sample plates 83 are arranged in an upright position, bowed or flexed as shown, FIG. 4 and frictionally retained within hollow frame 75 forming a part of the plate holder rack.

Each of the sample plates 83 are electrically non-conductive, being made of a plastic material and having a MYLAR (Trademark) backing, for illustration. Upon the opposite side of the plate is an electrophoresis media such as cellulose acetate. The electrophoresis media may be of other materials (agarose, cellulose esters, acrylamide gel, etc) which are known to be electrically conductive for use in the electrophoresis method, such as disclosed in U.S. Pat. No. 3,808,118 of Apr. 30, 1974 and issued to applicant's assignee, Helena Laboratories Corporation, Beaumont, Tex.

POWER OPERATED LIFT AND TRANSFER ASSEMBLY

The present lift and transfer assembly, FIGS. 1, 2 and 3 includes an electric motor 87, fragmentarily shown in FIG. 1, connected to the speed reducer 89, both mounted upon base 13, having an output shaft 91 mounting pulley 93 which by the belt 95 drives pulley 97 secured upon the elongated horizontal feed screw 99.

A pair of longitudinally spaced opposed journal blocks 101 are mounted and secured upon brackets 103, FIG. 1 and is secured by fasteners 105 to base 13. The horizontal feed screw 99 is supportably mounted and journalled upon said blocks and includes end thrust collar 107 in registry with one of the journal blocks.

A pair of horizontally disposed parallel spaced guide rods 109 are arranged upon opposite sides of the horizontal feed screw 99 and at their ends are anchored within corresponding apertures within said blocks.

Horizontally reciprocal feed block 111 has a pair of parallel spaced apertures 113 by which the block slidably receives the guide rods 109 and includes an interior threaded portion 115 in operative engagement with horizontal feed screw 99.

Belt drive motor 117 is supported upon and depends from support plate 119 secured to the undersurface of the feed block 111 and includes an output shaft 120 mounting pulley 122.

Journal block 121 is secured to one end of the horizontal feed block 111 by the anchor bracket 123 and journals and supports the vertical feed screw 125 having a thrust washer 127 in engagement with journal block 121 in order to maintain the upright position shown in FIG. 2.

Belt 129 interconnects pulley 122 and the pulley 133 upon the end of the vertical feed screw 125.

Vertical feed screw 125 receives and is threaded at 137 into the vertical feed block 135 upon which is mounted and secured the transverse plate holder support 139 which mounts and supports the plate holder rack 73 as shown in FIG. 2.

A pair of upright parallel spaced guide rods 141 loosely and guidably extend through the vertical feed block 135 and at their lower ends project into corresponding apertures within and are anchored upon journal block 121.

The upper journal block 121, FIGS. 1 and 2 is apertured to receive and be secured to the upper ends of the corresponding guide rods 141 and also journals the upper end of the vertical speed screw 125.

The mounting of the guide rods 141 and the corresponding vertical feed screw 125 upon the single journal block 121 is sufficient to maintain the members 141 and 125 in the upright position shown as movably mounted and supported upon the horizontal feed block 111. As shown in FIGS. 2 and 3, the down limit switch 145 is adjustably mounted upon and secured to one of the guide rods 141 in the path of downward movement of the vertically adjustable feed block 135 and is connected into the circuit with the motor 117 so as to deenergize the motor when the block 135 has reached the position shown in FIG. 2.

An up limit switch 147 is adjustably secured upon the other of the pair of upright guide rods 141. The limit switch 147 is in the path of upward movement of the vertical feed block 135 and is adapted to again de-energize the vertical feed motor 117, when it has reached its uppermost position as preset by the location of the uplimit switch 147. This automatically deactivates the vertical feed motor 117.

It is contemplated that the engagement of the upper limit switch 147 by the vertical feed block 135 could additionally energize the horizontal feed motor 87 to provide a horizontal intermittent feed to the horizontal feed block 111 with respect to the power rotated horizontal feed screw 99.

Motor 87 and the output shaft 91 from the connected speed reducer 89 will rotate causing continuous feed movement of the horizontal feed block 111 until the plate carrying rack 73 has been centralized with respect to the underlying vats successively 45, 47, 49, 51, 53 and 55 in a vertical stepping motion. Suitable stop means are thereby included for de-energizing the horizontal feed motor 87 at the appropriate period so that the plate carrying rack is in a central position overlying one of the said vats. Thereafter the vertical feed motor 117 is activated so as to cause a downward movement of the vertical feed block 135 lowering the rack and mounted plates 83 into the respective vats for immersion within the solutions therein.

The plate carrying rack 73 at all times maintains the plates 83 in an upright position so that after the initial electrophoresis process within container 25, the plates are lifted in a vertical plane by the lift and transfer assembly successively moved forward and thence downwardly into the next succeeding vat, such as vat 45 for immersion within the stain fluid therein.

After the initial electrophoresis process for a predetermined set interval, initial activation of the power operated lift and transfer unit and the energizing of the vertical feed motor 117 causes an upward movement of rack 73, mechanically disengaging the cover 31 from the resilient retractable hold down clips 35 with the cover opening to the dash line position shown in FIG. 1.

The movements of the plate carrying rack 73 which successively transfers the plates carried thereby from the electrophoresis chamber and for immersion successively and intermittently into the respective solution containing vats 45 through 55 as a linear stepping motion with the plates in the first instance transported from the electrophoresis chamber 27 into the fluid within the stain vat 45 for immersion therein for a predetermined interval. On successive lift and transfer movements, the stained plates are successively lifted, advanced and lowered into the respective solutions within the additional vats 47, 49, 51, 53 and 55.

METHOD OF ELECTROPHORESIS

The invention is further directed to the method of electrophoresis which includes the following steps:

1. Supporting in an upright position, a non-conductive plate 83 having on one surface an electrophoresis media to which has been applied a sample selected from the group consisting of serum proteins, lipoproteins, hemoglobins and isoenzymes, for example. The supporting of the plate or a plurality of such plates, employs a plate holder rack 73, FIG. 2, which includes the horizontally open frame 75 within which the plates are bowed and frictionally retained in the upright position shown. The plates 83 are supported for suspension within the electrophoresis chamber 27, FIG. 1.

2. A further step, includes the enclosing of said plate or plates within the chamber 27 by closing the cover 31 and thereafter applying an electrical potential to the plate ends within an electrical power circuit for a preselected period, at a preselected voltage, wherein the specimen elements fractionate and migrate laterally through portions of the electrophoresis media 85.

In the illustrative embodiment, the membrane is a cellulose acetate, but it could be made of other electrophoresis media, such as agarose, cellulose esters, acrylamide gel and other types for plate electrophoresis.

In the present method, the electrophoresis chamber 27 has a hinged cover 31 wherein the application of electrical potential includes the spaced electrical conductors 61 and 69 on the bottom of container 25 and upon cover 31.

3. The method includes the positioning of a buffer moistened conductive sponge 65 within a buffer solution 29, within the container to overlie the conductor 69 and thereafter the positioning of a second buffer moistened conductive sponge 57 depending from the cover in engagement with the second conductor 61. The method includes the positioning of the top and bottom edges of the plates 83 so as to be yieldably embedded into the surfaces of the respective sponges for completing the electrical circuit therethrough when the cover 31 is in the closed position shown in FIGS. 1 and 2.

The present method includes the use of a plate supporting and transfer rack 73 having an open framework 75 with the plates 83 horizontally bowed for frictional retention therein.

4. The present method includes the further step of elevating the plate or plates 83 after the electrophoresis process and translating the plates while maintaining them in an upright position and thereafter lowering the plates and immersing them within a stain solution of vat 45 for a predetermined interval.

5. The present method also includes in connection with the use of a power operated lift and transfer assembly 135, a means by which the plate holder rack 73 and the mounted plates 83 are successively transferred and immersed within their respective solutions in vats 45, 57, 49, 51, 53 and 55, for a predetermined period in a continuous linear stepping motion.

For the electrophoresis process, the technician pours a small amount of buffer solution 29, FIG. 1, into the bottom of chamber 27, being careful not to cover sponge 65. He then places the sample holder 73 with the sample plates 83 into the chamber 27. Rack 73 has a support 79 converted to the left and transfer unit. The plates 83 will push gently into the sponge 65 and will thus come into contact with the buffer solution therein. An additional electrode 61 is placed in contact with sponge 57. When the lid 31 is in the down position, its depending contact is in registry with a contact at the top of the chamber, which is electrically connected to conductor 69.

These six vats, preferably of plastic, are aligned with the electrophoresis chamber 27 upon the platform 23 so that the plates 83 can be immersed into each thereof in their proper order, i.e., dye for vat 45, rinse solution number 1 for vat 47, rinse solution number 2 for vat 49, rinse solution number 3 for vat 51, a fixative solution for vat 53 and a rinse for vat 55.

TRANSFER PROCESS

With the vat 73 loaded as in FIG. 4 with the plate or plates 83, vertical feed motor 117 is initially energized lowering the rack to the immersion position within the electrophoresis chamber until the vertical feed block 135 engages the down limit switch 145, FIG. 3.

After a predetermined preset interval including a timer within an electrical circuit to a power source, the vertical lift motor 117 is reactivated elevating the vertical feed block 135 and the rack 73, until it engages the uplimit switch 147 de-energizing the motor 117. At that time the horizontal feed motor 87 is automatically energized for a period until the loaded rack is transfered from the elevated position corresponding to FIG. 2 until it centrally overlies the first vat 45 and is automatically de-energized. In the electrical circuit the vertical feed motor 117 is energized so that its output shaft operates in the reverse direction rotating the vertical feed screw 125 and accordingly lowering the vertical feed block 135 and the connected rack and plate so as to be immersed within the solution in stain vat 45.

In accordance with a preset time, after a period of immersion, the vertical feed motor 117 is reactivated for drive in the opposite direction elevating the rack 73 to its uppermost position until the block 135 engages an uplimit switch 147. At that time, the horizontal feed motor is again energized for a period such as would feed the loaded rack to the next succeeding vat 47 centrally thereof, etc.

By this process, the loaded rack is advanced horizontally by the horizontal feed screw with interrupted longitudinal feed movements so that the rack centrally overlies the respective vats successively and is automatically lowered into the fluid therein and immersed for a predetermined period of time, and thereafter retracted and horizontally advanced to the next succeeding vat. Thus the loaded rack has been moved longitudinally with respect to the respective vats and has at each vat been lowered and immersed within the solution therein for a predetermined interval and thereafter elevated. The foregoing movements may be defined as a linear stepping motion.

STAINING COMPARTMENTS

In the illustrative embodiment, a stain referred to as "PONCEAU S" is employed within the stain vat 45 in a solution which is filled into the vat 45 to within 10 MM of the top to assure complete staining of the membranes.

The first rinsing compartment 47, for example, contains a solution of 5% GLACIAL acetatic acid. The second rinsing compartment 49 also contains a 5% GLACIAL acetatic acid. The third rinsing compartment 51 also contains the 5% GLACIAL acetatic acid.

The fixing vat 53 contains a methanol solution. The methanol dehydrates the plate or plates and removes the excessive water. The methanol should be changed daily or after dehydrating 10 plates. A contaminated methanol will create a cloudy background on a finished plate.

The clearing vat 55 contains a clearing solution which is composed of:
67 parts Methanol
28 parts Glacial Acetatic Acid
4 parts Clear Aid Helena (Catalogue No. 5005)
The clearing solution should be changed regularly to insure proper clearing of the cellulosic acetate. The clearing solution is used to soften the cellulose acetate membrane or other membrane employed.

LIPOPROTEIN ELECTROPHORESIS

The electrophoresis is employed in the chamber 27 using the same technique as would be employed for serum protein. To stain the lipoprotein plate, the operator must substitute for the Ponceau S in the chamber 45 with one filled with Oil Red Om and 1.0 normal sodium hydroxide.
330 mL Oil Red Om
110 mL 1.0 Normal Sodium Hydroxide
The lipoprotein plate can stain for a recommended time of 1 hour approximately.

HEMOGLOBIN ELECTROPHORESIS

This requires an offset application. Migration will be from the negative to the positive. Thus, the polarity switch, not shown, should be switched to positive. Staining, destaining and clearing of hemoglobins is identical to the serum protein format. Lipoproteins should be run at 180 volts for 25 minutes. The hemoglobins should be performed at 350 volts for 25 minutes.

Having described my invention, reference should now be had to the following claims.

I claim:
1. In an automated electrophoresis and staining apparatus;
an elongated base;
an elongated platform spaced from mounted on and overlying said base;
an electrophoresis chamber adapted to contain a buffer solution mounted upon said platform at one end thereof;
and a series of vats mounted upon said platform arranged in a row and aligned with said chamber, adapted to contain respectively a liquid stain and a series of processing solutions;
a plate holder rack including a horizontal open frame within said electrophoresis chamber and at one end a support arm projecting outwardly of said chamber;
said frame adapted for supporting one or a plurality of upright electrophoresis media plates onto which has been applied a sample for electrophoretic fractionization;
said plate or plates being nested within said chamber within an electrophoretic circuit between a cathode and anode for a predetermined period;
and a power operated lift and transfer assembly upon said base adapted to progressively lift, transfer and lower said plate holder and plates from said chamber and into each of said underlying vats successively for a predetermined period in a linear stepping motion;
whereby said plates in an upright position are immersed into the solutions within said vats.

2. In the electrophoresis apparatus of claim 1, said electrophoresis chamber including a cover pivoted upon and closing said chamber.

3. In the electrophoresis apparatus of claim 1, an elongated buffer moistened sponge underlying said sponge;

there being an elongated buffer moistened sponge within the bottom of said chamber;

said electrophoretic circuit including electrodes connected to a power source and in engagement with said sponges respectively, said sample mounted plates at their tops and bottoms being in engagement with said sponges for completing the circuit between said electrodes.

4. In the electrophoresis apparatus of claim 2, yieldable latches upon said chamber anchoring said cover in closed position when said rack is in its lower-most retracted position, upward movement of said rack lift and transfer assembly tilting said cover upwardly and out of the path of upward movement of said plate carrying rack.

5. In the electrophoresis apparatus of claim 1, said electrophoresis plates being arcuately flexed for upright frictional retention within said rack frame.

6. In the electrophoresis apparatus of claim 1, said lift and transfer assembly including a horizontal feed block guidably mounted upon said base for intermittent longitudinal movements;

the vertical feed block guidably mounted upon said horizontal feed block for reciprocal vertical feed movements;

and means connecting said rack to said vertical feed block;

said plates adapted for successive movements upwardly, forwardly and downwardly.

7. In the electrophoresis application of claim 6, said upward movement lifting said plateholder rack from said chamber, said forward movement transfering said rack to overlie the next adjacent vat;

said downward movement positioning said rack and plates within the solution in said vat.

8. In the electrophoresis apparatus of claim 1, said series of processing solutions including treating solutions 1, 2 and 3, a fixative solution and rinse solution.

9. In the electrophoresis apparatus of claim 6, the mounting of said horizontal feed block including a pair of longitudinally spaced journal blocks spaced from and mounted upon said base;

and a pair of parallel spaced guide rods extending between and at their ends connected to said journal blocks;

said horizontal feed block having a pair of spaced bores loosely receiving said guide rods respectively.

10. In the electrophoresis apparatus of claim 9, an elongated feed screw extending between and rotatably mounted upon said journal blocks;

said horizontal feed block having a threaded bore receiving said feed screw.

11. In the electrophoresis and staining apparatus of claim 9, the mounting of said vertical feed block including a pair of vertically spaced second journal blocks;

one of said blocks being mounted upon said horizontal feed block;

and a pair of parallel spaced upright guide rods extending between and at their ends connected to said second journal blocks;

the other of said second journal blocks being mounted upon said latter guide rods;

said vertical feed block having a pair of spaced bores loosely receiving said upright guide rods.

12. In the electrophoresis apparatus of claim 11, an elongated vertical feed screw extending between and rotatably mounted upon said second journal blocks;

said vertical feed block having a threaded bore receiving said vertical feed screw.

13. In the electrophoresis apparatus of claim 10, a first electric motor mounted upon said base having an intermittently rotatable drive shaft connected to said horizontal feed screw.

14. In the electrophoresis apparatus of claim 12, a second intermittently reversible electric motor mounted upon said horizontal feed block having a drive shaft connected to said vertical feed screw.

15. In the electrophoresis apparatus of claim 14, a pair of longitudinally spaced limit switches mounted upon said upright guide rods respectively, connected into an electrical circuit including said second motor, for alternately deactivating said motor at the top and bottom of predetermined vertical feed movements.

16. In the electrophoresis apparatus of claim 13, the connection between said first motor drive shaft and horizontal feed screw including a pair of pulleys on said motor drive shaft and horizontal feed screw respectively;

and a belt interconnecting said pulleys.

17. In the electrophoresis apparatus of claim 14, the connection between said second motor drive shaft and said vertical feed screw including a pair of pulleys mounted respectively on said latter motor drive shaft and vertical feed screw;

and a belt interconnecting said pulleys.

18. In the electrophoresis apparatus of claim 1, said support arm for said plate holder rack being L-shaped, having a vertical portion at one end connected to one end of said frame and a horizontal portion at one end connected to said vertical feed block for movement therewith.

19. In the electrophoresis apparatus of claim 9, the mounting of said vertical feed block including a pair of vertically spaced second journal blocks, one of said blocks being mounted upon said horizontal feed block;

and a pair of parallel spaced upright guide rods extending between and at their ends connected to said second journal blocks, the other of said second journal blocks being mounted upon said guide rods;

said vertical feed block having a pair of spaced bores loosely receiving said upright guide rods.

20. In the electrophoresis apparatus of claim 9, the mounting of said vertical feed block including a pair of vertically spaced second journal blocks;

one of said journal blocks being mounted upon said horizontal feed block;

and a pair of parallel spaced upright guide rods extending between and at their ends connected to said second journal blocks;

the other of said second journal blocks being mounted upon said upright guide rods, said vertical feed block having a pair of spaced bores loosely receiving said upright guide rods.

21. In the electrophoresis apparatus of claim 20, a first electric motor mounted upon said base having an intermittently operable drive shaft connected to said horizontal feed screw;

and a second intermittently reversible electric motor mounted upon said horizontal feed block having a drive shaft connected to said vertical feed screw.

22. In the electrophoresis apparatus of claim 21, a first electric motor mounted upon said base having an intermittently operable drive shaft connected to said horizontal feed screw;

and a second intermittently reversible electric motor mounted upon said horizontal feed block having a drive shaft connected to said vertical feed screw.

23. In the electrophoresis apparatus of claim 1, said plate selected from the group consisting of cellulose acetate, cellulose esters, agarose, acrylamide gel and any other media suitable for electrophoresis.

* * * * *